(12) United States Patent
Juranitch

(10) Patent No.: US 11,933,152 B2
(45) Date of Patent: Mar. 19, 2024

(54) METHOD, APPARATUS, AND SYSTEM FOR ENHANCED OIL AND GAS RECOVERY WITH SUPER FOCUSED HEAT

(71) Applicant: XDI Holdings, LLC, Bedford, NH (US)

(72) Inventor: James Charles Juranitch, Fort Lauderdale, FL (US)

(73) Assignee: XDI Holdings, LLC, Bedford, NH (US)

( * ) Notice: Subject to any disclaimer, the term of this patent is extended or adjusted under 35 U.S.C. 154(b) by 0 days.

(21) Appl. No.: 17/968,168

(22) Filed: Oct. 18, 2022

(65) Prior Publication Data

US 2023/0147037 A1    May 11, 2023

Related U.S. Application Data

(63) Continuation of application No. 17/242,842, filed on Apr. 28, 2021, now Pat. No. 11,506,036, which is a continuation of application No. 15/778,010, filed as application No. PCT/US2016/063339 on Nov. 22, 2016, now Pat. No. 11,021,941.

(60) Provisional application No. 62/258,512, filed on Nov. 22, 2015.

(51) Int. Cl.
   *E21B 43/24*     (2006.01)
   *C07C 5/333*     (2006.01)
   *C09K 8/592*     (2006.01)

(52) U.S. Cl.
   CPC .......... *E21B 43/2406* (2013.01); *C07C 5/333* (2013.01); *C09K 8/592* (2013.01); *E21B 43/24* (2013.01)

(58) Field of Classification Search
   CPC .......................... E21B 43/24; E21B 43/2406
   See application file for complete search history.

(56) References Cited

U.S. PATENT DOCUMENTS

| | | | |
|---|---|---|---|
| 3,150,716 A | 9/1964 | Samuel et al. | |
| RE27,252 E * | 12/1971 | Sklar et al. | E21B 43/243 166/263 |
| 4,641,710 A | 2/1987 | Klinger | |
| 2008/0289822 A1 | 11/2008 | Betzer Tsilevich | |
| 2010/0282644 A1 | 11/2010 | O'Connor et al. | |
| 2012/0103605 A1 | 5/2012 | Kuhlman | |
| 2012/0279292 A1 | 11/2012 | Simonian | |
| 2012/0325470 A1 | 12/2012 | Gupta et al. | |
| 2013/0175031 A1 | 7/2013 | Kerr | |
| 2013/0206399 A1 | 8/2013 | Pimenov et al. | |
| 2014/0020891 A1 | 1/2014 | Lamb et al. | |
| 2014/0231081 A1 | 8/2014 | Scinta et al. | |
| 2015/0198546 A1 | 7/2015 | Wang et al. | |
| 2015/0285048 A1 | 10/2015 | O'Donnell et al. | |
| 2017/0074082 A1 | 3/2017 | Palmer et al. | |

FOREIGN PATENT DOCUMENTS

WO    2015000066 A1    1/2015

* cited by examiner

*Primary Examiner* — Shane Bomar
(74) *Attorney, Agent, or Firm* — Dykema Gossett PLLC

(57) ABSTRACT

A system for improving a steam oil ratio (SOR) includes a boiler fluidly coupled with a downhole portion of a steam system via at least a boiler conduit, wherein the boiler is configured to schedule super-heat delivered to the downhole portion to optimize the SOR associated with the system.

20 Claims, 2 Drawing Sheets

METHOD, APPARATUS, AND SYSTEM FOR ENHANCED OIL AND GAS RECOVERY WITH SUPER FOCUSED HEAT

CROSS-REFERENCE TO RELATED APPLICATION

This application is a continuation of U.S. application Ser. No. 17/242,842, filed 28 Apr. 2021 (the '842 application), now U.S. Pat. No. 11,506,036, which is a continuation of U.S. application Ser. No. 15/778,010, filed 22 May 2018 (the '010 application), now U.S. Pat. No. 11,021,941, which is a national stage application of International patent application no. PCT/US2016/063339, filed 22 Nov. 2016 and published under International publication no. WO 2017/087989 A1 on 26 May 2017 (the '339 application). This application claims priority to U.S. provisional patent application No. 62/258,512, filed 22 Nov. 2015 (the '512 application). The '842 application, the '010 application, '339 application and the '512 application are all hereby incorporated by reference as though fully set forth herein

FIELD

Embodiments of the present disclosure generally relate to a method, apparatus and system for the optimization of oil and gas recovery using steam and super-heat.

DESCRIPTION OF THE RELATED ART

Many steam boilers are used in the oil and gas recovery world such as Once Through Steam Generators (OTSG) and Drum Boilers. To date, much art has been published using these steam boilers to generate a saturated steam for enhanced oil and gas recovery.

SUMMARY

Various embodiments of the present disclosure can include a system for improving a steam oil ratio (SOR). The system can include a boiler fluidly coupled with a downhole portion of a steam system via at least a boiler conduit. In some embodiments, the boiler can be configured to schedule super-heat delivered to the downhole portion to optimize the SOR associated with the system.

Various embodiments of the present disclosure can include a method for improving the SOR. The method can include providing super-heat with at least one of a boiler and a super-heater fluidly coupled in series with a downhole portion of a steam system to the downhole portion of the steam system. The boiler can be fluidly coupled with the super-heater via a boiler conduit and the super-heater can be fluidly coupled with the downhole portion of the steam system via a super-heater outlet conduit. In some embodiments, the method can include determining whether a condensate loss from the super-heater outlet conduit is greater than a defined value. In some embodiments, the method can include adjusting the amount of super-heat based on the determination of whether the condensate loss from the super-heater outlet conduit is greater than the defined value.

Various embodiments of the present disclosure can include a system for improving the SOR. In some embodiments, the system can include a boiler. A super-heater can be fluidly coupled with the boiler via a boiler conduit. The boiler and the super-heater can both be configured to produce an amount of super-heat. In some embodiments, a downhole portion of a steam system can be fluidly coupled with the super-heater via a super-heater outlet conduit and the downhole portion of the steam system can include a horizontal pipe section. In some embodiments, a collection pipe can be disposed adjacent to the horizontal pipe section and configured to collect mobilized oil and spent steam and return the mobilized oil and spent steam to a ground surface location. In some embodiments, the SOR can be measured at the ground surface location.

DETAILED DESCRIPTION

Figure 1:
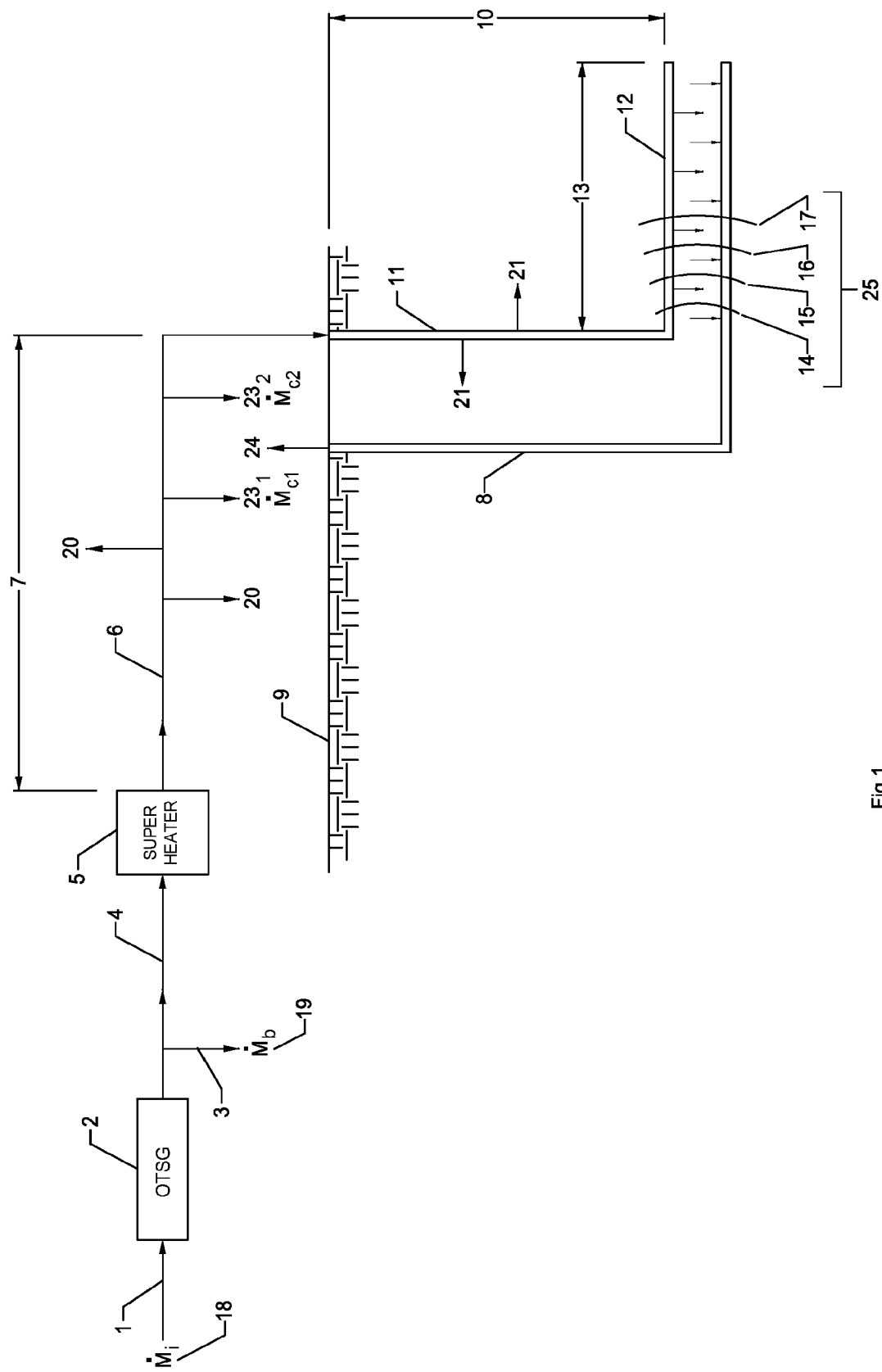
FIG. 1 depicts a system and apparatus for enhanced oil and gas recovery with super focused heat, in accordance with embodiments of the present disclosure.

In enhanced oil and gas recovery, steam is many times utilized. This could include Steam Assisted Gravity Drain (SAGD), Cyclic Steam Stimulation (CSS) and other types of oil and gas recovery. To date, a steam boiler is utilized to generate a saturated steam, which can then be directed to melt out or mobilize the oil and gas in underground deposits. Typically, a Once Through Steam Generator (OTSG) or a Drum Boiler can be used to generate the steam, which is often saturated steam. The steam can then be pumped through a series of conduits or pipes eventually traveling underground to the desired heavy oil or other desired deposit. The steam in most cases can be generated as saturated steam product at the outlet of the boiler. The saturated steam can then be directed through the balance of the oil or gas recovery system. Much heat and steam energy can be lost in the process without the benefit of producing a product such as bitumen or heavy oil. The industry keeps score on a site's oil recovery efficiency with a Steam Oil Ratio (SOR). The SOR simply logs the metric of how many barrels of water in the form of steam are required to net a barrel of oil. SORs can range from approximately 2 to 6. All sites and operators desire the lowest operating SOR possible. The SOR at a site directly relates to the cost of oil recovery.

Steam in its many forms has different heat transfer characteristics/coefficients. These heat transfer coefficients then directly relate to the amount of heat energy transferred from the steam as it passes through a system or pipe. The amount of heat energy transferred can vary dramatically. For example, at a given steam pressure and temperature, the heat energy transferred through a pipe can range from a factor of 1 for super-heated steam to an approximate factor of 10 for saturated steam to a factor of 4 for condensate. Embodiments of the present disclosure can use that characteristic of steam to minimize the amount of steam energy that is currently being wasted in existing enhanced oil or gas recovery systems. Embodiments of the present disclosure can utilize a mathematical model (implemented, for example, in the software or firmware of a control system) to schedule the super-heated steam. Embodiments of the present disclosure can utilize a feedback in the form of the SORs (e.g., determined in part via condensate accumulation) for continuous improvement or Kaizen in the mathematical model and oil recovery site.

Embodiments of the present disclosure can improve the efficiency of an enhanced oil or gas recovery site. As an example, Steam Assisted Gravity Drain (SAGD) will be used to describe at least one embodiment of the present disclosure. Embodiments of the present disclosure are able to be used to optimize any steam system or enhanced oil or gas recovery process.

Embodiments of the present disclosure include a system, method, and apparatus comprising a boiler and an optional super-heater. Super-heated steam can be generated and utilized for enhanced oil and gas recovery. The scheduling and optimization of the super-heated steam can be scheduled or controlled by a mathematical model. The scheduling and mathematical model can be continuously improved through an iterative process using multiple feedbacks, such as condensate flow, process temperature, process pressures, process flows, system energy and SOR for optimization.

FIG. 1 depicts a system and apparatus for enhanced oil and gas recovery with super focused heat, in accordance with embodiments of the present disclosure. As depicted in FIG. 1, water can be injected into a boiler 2 via an inlet tube 1 with a first mass flow 18 (depicted as $M_i$). In some embodiments of the present disclosure, mass flow can be measured at any location via a positive displacement meter with or without numerical mass correction, a turbine flow meter with or without numerical correction, a hot wire mass flow measurement, a Coriolis flow meter, a column and float system, or settling tanks and scale measurement, an orifice plate system, which are only a few examples of how mass flow can be measured as known by those skilled in the art. The inlet tube 1 can be fluidly coupled with the boiler 2. The water can be processed by the boiler 2. In some embodiments, the boiler 2 can be a OTSG, as depicted in FIG. 1. An amount of blow down 3, with a second mass flow 19 (depicted as $M_b$) can be typical in a conventional steam system. The resulting mass flow of the steam at location 4, which in many cases is at saturated conditions, but not limited to saturated conditions, is transferred into the super-heater 5. As depicted in FIG. 1, the boiler 2 can be fluidly coupled with the super-heater 5 via a boiler conduit. The super-heater 5 can be powered by natural gas or any other energy sources. Super-heater outlet conduit 6 can have a super-heater outlet length represented by line 7. The super-heater outlet conduit 6 can be used to direct the steam to a down hole portion of the enhanced oil site. In some embodiments, heat can be lost from the super-heater outlet conduit 6. Such heat loss is depicted as outlet heat loss 20. In some embodiments, condensate can be lost from the super-heater outlet conduit 6. Such condensate loss is depicted as outlet condensate loss $23_1$, $23_2$ with a given total mass flow (depicted as $M_{c1}$, $M_{c2}$).

The super-heater outlet conduit 6 can be fluidly coupled to a down hole portion 11 of the steam system. In some embodiments, the down hole portion 11 of the steam system can have a down hole portion length represented by line 10. In some embodiments, heat can be lost from the down hole portion 11. Such heat loss is depicted as down hole heat loss 21. Horizontal pipe section 12 in the oil recovery section of a SAGD system can include a perforated pipe system (e.g., perforated pipe section) that expels steam into the oil deposits to mobilize heavy oil (e.g., subterranean heavy oil) and can have a length represented by line 13. Although the horizontal pipe section 12 is described as horizontal, the horizontal pipe section 12 can be disposed at a non-horizontal angle. In some embodiments, the perforated pipe system can ideally expel saturated steam with its superior heat energy being transferred into the oil deposits to mobilize the heavy oil. In an example, the heavy oil can melt out of formations in a continually expanding arc (e.g., melt out of formations located close to and away from the horizontal pipe section 12) as depicted by arced lines 14, 15, 16, 17, etc. eventually making a chamber 25. The mobilized oil and spent (e.g., condensated) steam is then collected in collection pipe 8, which is configured to collect the mobilized oil and spent steam, and lifted to the surface of the ground 9 to ground surface location 24 via the collection pipe 8 for further processing and eventual sale. As depicted, the collection pipe 8 can be disposed adjacent to the horizontal pipe section 12. In some embodiments, the collection pipe 8 can be disposed substantially parallel with the horizontal pipe section 12.

Embodiments of the present disclosure can provide for the addition of super-heat by any method at an optional super-heater 5 and potentially at boiler 2 to increase the energy of the steam and optimize the amount of super-heat in the steam to allow the mass flow to ideally be converted to saturated steam at and/or in horizontal pipe section 12 and ideally at the location of new work or heat transfer into the ever expanding chamber 25 for the mobilization of the bitumen at locations depicted by arced lines 14, 15, 16, 17, etc. As the heat loss and condensate loss is minimized in, for example, super-heater outlet conduit 6 and down hole portion 11 and the saturated steam is allowed to effectively deliver its stored energy to the bitumen at locations depicted by arced lines 14, 15, 16, 17, etc. and generally chamber 25, the SOR will be improved and reduced numerically.

The amount of super-heat (e.g., the addition of super-heat by any method at optional super-heater 5 and potentially at boiler 2) can be scheduled by many mathematical models in many embodiments. In some embodiments, a feedback control can be employed to increase an amount of super-heat until a mass flow of outlet condensate loss $23_1$, $23_2$ ($M_{c1}$+$M_{c2}$) is reduced to 0. In some embodiments, an amount of super-heat can be increased until a mass flow of outlet condensate loss $23_1$, $23_2$ is within a defined threshold of 0. Upon reducing a mass flow at outlet condensate loss $23_1$, $23_2$ to 0 (or within a defined threshold of 0) the model in this example can continue to increase super-heat until the SOR is minimized, which can be used for continuous iterations and improvements in efficiency, or Kaizen. Upper limits of super-heated steam temperature boundary conditions can be employed.

In some embodiments, the feedback control can be implemented via a computing device, which can be a combination of hardware and instructions to share information. The hardware, for example can include a processing resource and/or a memory resource (e.g., computer-readable medium (CRM), database, etc.). A processing resource, as used herein, can include a number of processors capable of executing instructions stored by the memory resource. The processing resource can be integrated in a single device or distributed across multiple devices. The instructions (e.g., computer-readable instructions (CRI)) can include instructions stored on the memory resource and executable by the processing resource to implement a desired function (e.g., increase super-heat, etc.).

The memory resource can be in communication with the processing resource. The memory resource, as used herein, can include a number of memory components capable of storing instructions that can be executed by the processing resource. Such memory resource can be a non-transitory CRM. The memory resource can be integrated in a single device or distributed across multiple devices. Further, the memory resource can be fully or partially integrated in the same device as the processing resource or it can be separate but accessible to that device and processing resource. Thus, it is noted that the computing device can be implemented on a support device and/or a collection of support devices, on a mobile device and/or a collection of mobile devices, and/or a combination of the support devices and the mobile devices.

The memory can be in communication with the processing resource via a communication link (e.g., path). The communication link can be local or remote to a computing device associated with the processing resource. Examples of a local communication link can include an electronic bus internal to a computing device where the memory resource is one of a volatile, non-volatile, fixed, and/or removable storage medium in communication with the processing resource via the electronic bus.

An example of an additional embodiment of a mathematical model embodiment to schedule the amount of super-heat can start with the same previously described model minimizing condensate flow and then continue to derive a coefficient "a" times super-heat quantity x, times the first mass flow 18 minus the second mass flow 19. Coefficient "a" can be derived from the terms of a total of the derived heat loss of super heater outlet conduit 6 determined through analytical means or empirical pipe section temperature measurements (delta temperatures) per distance c, times superheater outlet length 7, plus the derived heat loss of down hole portion 11 determined through analytical means or empirical pipe section temperature measurements (delta temperatures) per distance d, times down hole portion length 10, plus a distance unit of measure, times volume of chamber 25, times a coefficient. In some embodiments, the distance unit of measure can be a length of the horizontal pipe section 12 (e.g., that is in active communication with a bitumen product), potentially represented by line 13. Again the SOR at ground surface location 24 can be used as a feedback or metric to continuously iterate and optimize the level of superheat injected and continuously optimize the system or employ the principals of Kaizen. For example, the SOR can be measured at the ground surface location 24. Again, upper limits of super-heated steam temperature boundary conditions can be employed. Process temperature feedbacks such as system pipe temperatures, process flows, process pressure feedbacks, system energy flow and many other feedbacks can be incorporated into ever exacting models with higher levels of sophistication to accurately schedule the optimum super-heat. Condensate flow and SOR are only two examples of feedbacks used in embodiments of the present disclosure.

Figure 2:
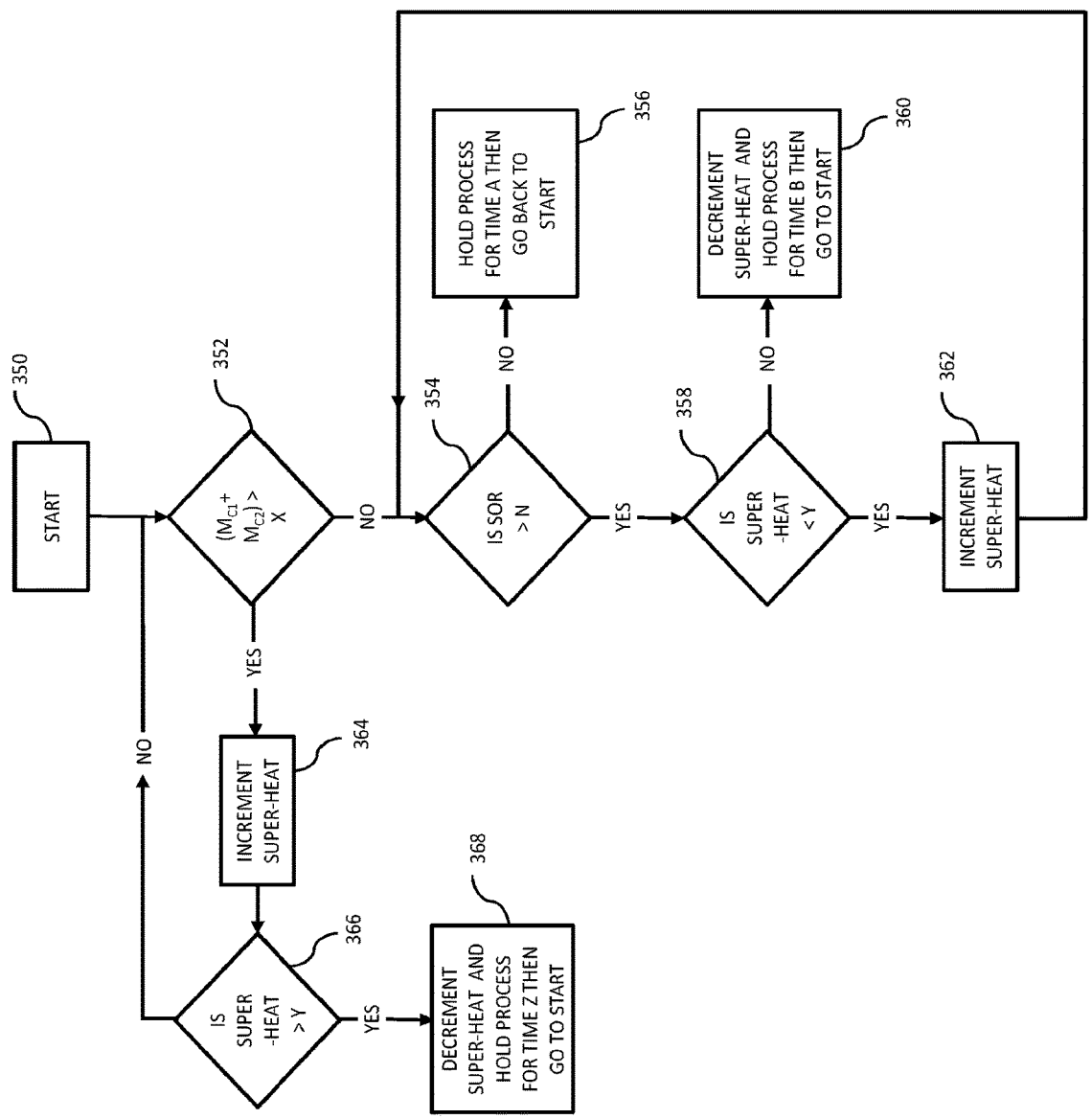
FIG. 2 depicts a flow chart associated with feedback control for controlling super-heat, in accordance with embodiments of the present disclosure.

FIG. 2 depicts a flow chart associated with feedback control for controlling super-heat, in accordance with embodiments of the present disclosure. In some embodiments, each block of the flow chart can represent an instruction, executable by a processor, as discussed herein. In some embodiments, each block of the flow chart can represent a method step, as discussed herein. The flow chart is depicted as starting at block 350. At decision block 352, a determination can be made of whether the outlet condensate loss $23_1$, $23_2$ with total mass flow ($M_{c1}+M_{c2}$), or any singular condensate flow measurement, (depicted in FIG. 1) is greater than a value X. The value X can be a measured numerical value associated with total mass flow ($M_{c1}+M_{c2}$), or any singular condensate flow measurement, (e.g., measured in a manner analogous to that discussed herein). In some embodiments, the value X can be 0. However, the value X can be greater than 0, for example, a value that is close to 0 and/or within a defined threshold of 0. As previously discussed, as condensate loss is minimized in the super-heater outlet conduit 6 (depicted in FIG. 1), the saturated steam can be allowed to effectively deliver its stored energy to the bitumen and the SOR can be improved and reduced numerically. Thus, while it is not necessary that the value X be 0, efficiency of the system can be increased as the value X approaches 0. For example, the value X can be less than or equal to 1 gallon per hour (e.g., the value X can be in a range from 0 to 1 gallons per hour). However, the value X can be greater than 1 gallon per hour.

As depicted in FIG. 2, in response to a determination that the total mass flow ($M_{c1}+M_{c2}$), or any singular condensate flow measurement, is less than the value X (e.g., NO), control can be transferred to decision block 354, where a determination can be made of whether the SOR is greater than a value N (e.g., defined SOR value). The value N can be a determined numerical value associated with the SOR. In some embodiments, the value N can be defined by a user (e.g., received from a user via a user interface in communication with the computing device) and can be representative of a desired SOR. In response to a determination that the SOR is less than the value N (e.g. NO), control can be transferred to block 356, which can include an executable instruction to hold process for time A and then proceed to start at block 350. For example, block 356 can include an instruction to maintain a constant generation and/or temperature of super-heat (e.g., to not decrease or increase super-heat and/or to not decrease or increase super-heat outside of a defined range) for a particular time A. In some embodiments, the particular time A can be defined by a user. The particular time A can be 0 in some embodiments or a value greater than 0 (e.g., 1 second, 20 seconds, 3 minutes, 3 days, etc.). Upon the expiration of time A, the process can proceed to start block 350.

In response to a determination that the SOR is greater than the value N (e.g. YES), control can be transferred to decision block 358, where a determination can be made of whether a particular amount of super-heat generated and/or a temperature of the super-heat is less than a numerical value Y, which can be defined by a user. In some embodiments, the numerical value Y can be representative of an upper limit of a super-heated steam temperature boundary condition, as discussed herein. In response to a determination that the particular super-heat is greater than the value Y (e.g., NO), control can be transferred to block 360, which can include an executable instruction to decrement (e.g., decrease via a feedback control) super-heat and hold process for time B, then proceed to start. For example, block 360 can include an instruction to decrement a generation and/or temperature of super-heat for a particular time B. The particular time B can be a value greater than 0 (e.g., 1 second, 20 seconds, 3 minutes, 3 days, etc.). Upon the expiration of time B, the process can proceed to start block 350.

As depicted in FIG. 2, in response to a determination that the particular super-heat is less than the value Y (e.g., YES), control can be transferred to block 362, which can include an executable instruction to increment (e.g., increase) super-heat. For example, block 362 can include an instruction to increment an amount and/or temperature of super-heat generated. In some embodiments, the amount and/or temperature of super-heat generated can be incremented for a defined time before control is transferred back to decision block 354.

As depicted in FIG. 2, in response to a determination that the total mass flow ($M_{c1}+M_{c2}$), or any singular condensate flow measurement, is greater than the value X (e.g., YES), control can be transferred to block 364, which can include an executable instruction to increment super-heat. For example, block 364 can include an instruction to increment an amount and/or temperature of super-heat generated. In some embodiments, the amount and/or temperature of super-heat generated can be incremented for a defined time before control is transferred back to decision block 366.

At decision block 366, a determination can be made of whether a particular amount of super-heat generated and/or a temperature of the super-heat is greater than the numerical value Y (e.g., defined super-heat value), which can be defined by a user. In some embodiments, the numerical value Y can be representative of an upper limit of a super-heated steam temperature boundary condition, as discussed herein. In response to a determination that the particular super-heat is greater than the value Y (e.g., YES), control can be transferred to block 368, which can include an executable instruction to decrement super-heat and hold process for time Z, then proceed to start. For example, block 368 can include an instruction to decrement a generation and/or temperature of super-heat for a particular time Z. The particular time Z can be a value greater than 0 (e.g., 1 second, 20 seconds, 3 minutes, 3 days, etc.). Upon the expiration of time B, the process can proceed to start block 350. As discussed herein, a generation and/or temperature of super-heat can be incremented or decremented via use of feedback control, which can be implemented with the assistance of a feedback controller, such as a PID controller.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be further appreciated that for conciseness and clarity, spatial terms such as "vertical," "horizontal," "up," and "down" may be used herein with respect to the illustrated embodiments. However, these terms are not intended to be limiting and absolute.

Although at least one embodiment for a method, apparatus, and system for enhanced oil and gas recovery with super focused heat has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention claimed is:

1. A method for controlling super-heat, comprising:
providing an amount of superheat to a downhole portion of a steam system via an outlet conduit; and
adjusting the amount of superheat based on an amount of condensate loss from the outlet conduit.

2. The method of claim 1, wherein adjusting the amount of superheat based on the amount of condensate loss includes adjusting the amount of superheat in response to the condensate loss being greater than a defined condensate loss value.

3. The method of claim 2, wherein the amount of condensate loss is measured as a singular condensate flow measurement of the steam system.

4. The method of claim 2, wherein the amount of condensate loss is measured as a total condensate flow measurement of the steam system.

5. The method of claim 1, further comprising adjusting the amount of superheat to minimize the amount of condensate loss from the outlet conduit.

6. The method of claim 1, further comprising determining whether a steam oil ratio is greater than a defined steam oil ratio threshold when the amount of condensate loss is less than a defined amount of condensate loss.

7. The method of claim 6, further comprising maintaining a constant generation of super-heat in response to the steam oil ratio being less than the defined steam oil ratio threshold.

8. The method of claim 6, further comprising determining whether the amount of super-heat is less than a defined super-heat value in response to the steam oil ratio being greater than the defined steam oil ratio threshold.

9. The method of claim 8, further comprising decrementing the amount of super-heat in response to the amount of super-heat being less than the defined super-heat value.

10. The method of claim 8, further comprising incrementing the amount of super-heat in response to the amount of super-heat being greater than the defined super-heat value.

11. The method of claim 10, further comprising determining whether the steam oil ratio is greater than the defined steam oil ratio threshold in response to incrementing the amount of super-heat.

12. The method of claim 1, further comprising incrementing the amount of superheat in response to the condensate loss from the outlet conduit being greater than a defined amount of condensate loss.

13. The method of claim 12, further comprising determining whether the amount of superheat is greater than a defined amount of super-heat, in response to incrementing the amount of superheat.

14. The method of claim 13, further comprising decrementing the amount of super-heat to a reduced amount of super-heat for a defined time, in response to the amount of super-heat being greater than the defined amount of super-heat, before determining a second amount of condensate loss from the outlet conduit.

15. A method for controlling super-heat, comprising:
providing an amount of superheat to a downhole portion of a steam system via an outlet conduit; and
increasing the amount of superheat in response to an amount of condensate loss from the outlet conduit exceeding a threshold.

16. The method of claim 15, further comprising increasing the amount of superheat via a feedback controller.

17. The method of claim 16, further comprising providing a feedback to the controller that includes the amount of condensate loss.

18. A method for controlling super-heat, comprising:
providing an amount of superheat to a downhole portion of a steam system via an outlet conduit; and
decreasing the amount of superheat in response to an amount of condensate loss from the outlet conduit dropping below a threshold.

19. The method of claim 18, wherein the amount of superheat is decreased to a threshold level.

20. The method of claim 19, wherein the amount of superheat is decreased and held constant for a particular period of time, in response to the amount of superheat exceeding the threshold level.

\* \* \* \* \*